(12) United States Patent
Thomas et al.

(10) Patent No.: US 11,607,379 B2
(45) Date of Patent: Mar. 21, 2023

(54) COMPOSITION FOR COMBATING THE SIGNS OF AGEING OF THE SKIN AND HAIR AND NAILS

(71) Applicant: TOMCAT INTERNATIONAL, London (GB)

(72) Inventors: Bertrand Thomas, Paris (FR); Mathilde Thomas, Paris (FR)

(73) Assignee: TOMCAT INTERNATIONAL

( * ) Notice: Subject to any disclaimer, the term of this patent is extended or adjusted under 35 U.S.C. 154(b) by 296 days.

(21) Appl. No.: 16/314,521

(22) PCT Filed: Sep. 12, 2016

(86) PCT No.: PCT/FR2016/052294
§ 371 (c)(1),
(2) Date: Dec. 31, 2018

(87) PCT Pub. No.: WO2018/002453
PCT Pub. Date: Jan. 4, 2018

(65) Prior Publication Data
US 2019/0201318 A1    Jul. 4, 2019

(30) Foreign Application Priority Data

Jul. 1, 2016   (FR) ..................... 1656318

(51) Int. Cl.
| | | |
|---|---|---|
| A61K 8/9767 | (2017.01) | |
| A61K 36/87 | (2006.01) | |
| A61K 8/34 | (2006.01) | |
| A61Q 19/08 | (2006.01) | |
| A61K 36/15 | (2006.01) | |
| A61K 8/97 | (2017.01) | |
| A61K 8/9789 | (2017.01) | |
| A61P 39/06 | (2006.01) | |
| A61K 8/49 | (2006.01) | |
| A61K 31/05 | (2006.01) | |
| A61K 31/09 | (2006.01) | |
| A61K 31/341 | (2006.01) | |
| A61K 31/355 | (2006.01) | |
| A61K 31/365 | (2006.01) | |
| A61K 31/366 | (2006.01) | |

(52) U.S. Cl.
CPC ............ *A61K 8/9767* (2017.08); *A61K 8/347* (2013.01); *A61K 8/498* (2013.01); *A61K 8/4973* (2013.01); *A61K 8/97* (2013.01); *A61K 8/9789* (2017.08); *A61K 31/05* (2013.01); *A61K 31/09* (2013.01); *A61K 31/341* (2013.01); *A61K 31/355* (2013.01); *A61K 31/365* (2013.01); *A61K 31/366* (2013.01); *A61K 36/15* (2013.01); *A61K 36/87* (2013.01); *A61P 39/06* (2018.01); *A61Q 19/08* (2013.01)

(58) Field of Classification Search
None
See application file for complete search history.

(56) References Cited

U.S. PATENT DOCUMENTS 6,579,543 B1 * 6/2003 McClung ............. A61K 36/886
424/728
2010/0047294 A1   2/2010 Ahlnas

FOREIGN PATENT DOCUMENTS

| EP | 0698595 A1 | 2/1996 |
| FR | 3017289 A1 | 8/2015 |
| JP | 2003160433 A | 6/2003 |
| WO | 2009101261 A2 | 8/2009 |
| WO | 2011128714 A1 | 10/2011 |

OTHER PUBLICATIONS

Mintel. CVS Pharmacy: "Accelerated Wrinkle Repair Moisturizer", XP002764745, product description and ingredients, Dec. 1, 2015, 4 pages.
Mintel—Caudalie: "Eye Lifting Balm", XP002764744, product description and ingredients. Feb. 1, 2016, 7 pages.
Bjarne Holmborn, et al., "Knots in trees—A new rich source of lignans", Phytochemistry Reviews 2: 331-340, 2003.
The Canadian Intellectual Property Office (CIPO), Council of Scientific & Industrial Research (CSIR), Traditional Knowledge Digital Library Unit (TKDL), Third Party Observation, dated Oct. 22, 2019, Publication No. WO2018/002453 and CIPO acknowledgments of prior art and exhibits, 22 pages.

* cited by examiner

*Primary Examiner* — Susan Hoffman
(74) *Attorney, Agent, or Firm* — St. Onge Steward Johnston & Reens LLC

(57) ABSTRACT

A composition for topical application containing at least one combination of (a) polyphenols selected from proanthocyanidin monomers and oligomers (OPC), hydroxystilbenes, flavonoid monomers and oligomers, and derivatives and mixtures thereof, (b) a spruce extract having at least one lignan selected from: hydroxymatairesinol, secoisolariciresinol, conidendrin, lariciresinol and liovile. It also relates to the cosmetic use of such a combination for combating the signs of ageing of the skin or hair and nails or the effects of pollution, and a cosmetic treatment method using said combination.

20 Claims, No Drawings

COMPOSITION FOR COMBATING THE SIGNS OF AGEING OF THE SKIN AND HAIR AND NAILS

FIELD OF THE INVENTION

The present invention relates to cosmetic compositions and combinations of active agents which improve the appearance of the skin or of the skin appendages and are in particular of use as agents for combatting certain signs of aging of the skin or of the skin appendages and/or as anti-pollution agents.

The invention relates in particular to combinations which reinforce the intrinsic defenses of the skin against oxidizing agents. It also relates to the cosmetic use thereof for combatting the signs of aging of the skin or of the skin appendages, for improving the radiance of the complexion or for reducing dark circles under the eyes. It also relates to a cosmetic treatment process comprising the topical application of the combination or of a composition containing same.

BACKGROUND OF THE INVENTION

The skin consists of two compartments, a superficial one, the epidermis, and a deeper one, the dermis, which interact. The human epidermis is composed mainly of three types of cells, which are the keratinocytes, that are very predominant, the melanocytes and the Langerhans cells. Each of these cell types contributes by virtue of its own functions to the role of the skin in the organism, and in particular to the protection against outside attacks.

The epidermis is conventionally divided up into a basal layer of keratinocytes constituting the germinative layer of the epidermis, a layer, termed spiny layer, consisting of several layers of polyhedral cells placed on the germinative layers, one to three layers, termed granular layers, consisting of flattened cells containing distinct cytoplasmic inclusions, which are the keratohyalin granules, and finally the horny layer (or stratum corneum), consisting of a set of layers of keratinocytes at the terminal stage of their differentiation, called corneocytes.

The dermis gives the epidermis a solid support. It is also its feeder element. It consists mainly of fibroblasts and of an extracellular matrix composed mainly of collagen, of elastin and of a substance termed ground substance. These components are synthesized by the fibroblasts. Leukocytes, mast cells or else tissue macrophages are also found therein. Finally, blood vessels and nerve fibers pass through the dermis.

The cohesion between the epidermis and the dermis is ensured by the dermoepidermal junction.

Cellular oxidation and free-radical accumulation play an important role in aging processes.

The sources of free radicals may be endogenous, resulting from normal metabolic processes or from respiration; they may also be increased by environmental factors such as exposure to pollution, to smoke or to UV rays. The action of these free radicals on the skin can lead to oxidative stress.

These aging phenomena, whether they are of intrinsic or extrinsic origin, are natural physiological phenomena. However, there is still a need, for a large number of men and women, to improve the appearance of their skin or of their skin appendages and to reduce or delay the signs associated with aging.

Application JP2003160433 describes complex compositions with anti-MMP (matrix metalloproteinase) activity containing a mixture of *Theobroma cacao* with various plant extracts.

The cells, in particular cutaneous cells, have developed defense mechanisms against these oxidizing agents and oxidative stress, and for preventing the adverse effects thereof which contribute to aging.

This involves, on the one hand, glutathione, in its reduced form; on the other hand, numerous enzymes have antioxidant activity, such as superoxide dismutases (SODs), catalases, or heme oxygenases.

The use of antioxidants has already been proposed in the cosmetics field, in particular in topical application. Tocopherol (vitamin E) or derivatives thereof, vitamin C or derivatives thereof, carotenoids, ubiquinone or green tea are for example known.

Application FR 3 017 289 describes compositions with a strong direct antioxidant capacity containing derivatives of polyphenols and of vitamin C.

However, there is still a need to have available new active agents capable of exerting an overall antioxidant cosmetic action and in particular of combatting oxidative stress of the skin and/or the hair and the effects thereof.

SUMMARY OF THE INVENTION

It has now been found, in the context of the present invention, that extracts of the plant *Picea abies* which have a direct antioxidant activity are also capable of promoting the two endogenous defense pathways of cells against oxidative stress.

In addition, the antioxidant effect on the cell defenses is synergistically increased when these extracts are combined with polyphenols of the type of those present in vine; these polyphenols may be in native or stabilized form.

For this reason, a subject of the present invention is a combination of (a) at least one polyphenol chosen from proanthocyanidin monomers and oligomeric proanthocyanidins (OPCs), hydroxystilbenes, flavonoid monomers and oligomers, derivatives thereof and mixtures thereof, and (b) a spruce extract comprising at least one lignan chosen from: hydroxymataíresinol, secoisolariciresinol, conidendrin, lariciresinol and liovil.

A subject of the invention is also compositions, in particular compositions for topical application such as cosmetic compositions, containing at least said combination.

A subject of the invention is also the combinations as defined in the present application, or compositions containing same, for use thereof for preventing or decreasing skin disorders linked to oxidative stress, and/or for stimulating the defenses of cutaneous cells against oxidative stress.

A subject of the invention is also the nontherapeutic cosmetic use of a combination of (a) at least one polyphenol chosen from proanthocyanidin monomers and oligomeric proanthocyanidins (OPCs), hydroxystilbenes, flavonoid monomers and oligomers, derivatives thereof and mixtures thereof, and (b) a spruce extract comprising at least one lignan chosen from hydroxymataíresinol, secoisolariciresinol, conidendrin, lariciresinol and liovil, or of a cosmetic composition containing same, for combatting the signs of aging of the skin or of the skin appendages and/or combatting the cutaneous signs linked to the environment and in particular to pollution.

The invention also relates to the use of a spruce (or *Picea abies*) extract for stimulating the endogenous defenses of cutaneous cells and for improving the resistance of cutaneous cells to oxidative stress. The *Picea abies* extract will be of use as an agent for these applications and in particular in combinations or compositions containing same and aimed at improving the resistance of the skin to oxidative stress, for combatting the signs of aging or for improving the radiance of the skin.

DETAILED DESCRIPTION

*Picea abies* (or spruce) extracts that are of use according to the invention have been described in application WO 2009/101261, for their antibacterial activity and as photoprotective agents in anti-UV products. The activity of these extracts is based mainly on an oxidation-reduction reaction which makes it possible to neutralize the free radicals, or by trapping these radicals.

Unexpectedly, it has now been found that *Picea abies*, or spruce, extracts increase GSH production by cutaneous cells and thus improve their resistance and that of the skin to oxidative stress.

Glutathione is an antioxidant present in cells in the basal state, mainly in reduced form, GSH. A small fraction is in oxidized form, GSSG. The spruce extracts according to the invention are capable of increasing GSH synthesis by at least 10% compared with cutaneous cells which have not been in contact with said extract; this increase may be at least 20%, or even at least 30%, and may be greater than or equal to 60%, and in particular equal to approximately 66%.

In addition, the spruce extracts according to the invention activate, at non-toxic doses, the cellular synthesis of the heme oxygenase 1 or HO-1 enzyme.

Heme oxygenase is an enzyme involved in hemoglobin degradation. Heme oxygenase isoform 1 (HO-1) is a phase-II enzyme present in normal human skin; it plays a role in the physiological system of detoxification of the skin and of antioxidant protection, in response to stimuli such as oxidative stress.

A spruce extract is therefore of use for promoting the endogenous defenses of the skin against oxidizing species, via two complementary pathways.

It has moreover been discovered, in the context of the present invention, that polyphenols, in particular polyphenols extracted from vine, or derivatives thereof, also have a stimulatory effect on synthesis of the HO-1 enzyme.

Unexpectedly, a combination of spruce extract and of polyphenols extracted from vine or of derivatives of polyphenols extracted from vine has a synergistic effect on the increase in HO-1 production (synthesis) by the cells, in particular the cells of the skin.

The combination of a spruce extract and of polyphenols, in particular of polyphenols extracted from vine or of derivatives of such polyphenols will therefore have an improved activity in stimulating the endogenous defenses of the cutaneous cells against oxidizing species at two complementary levels, via the glutathione pathway (increase in GSH synthesis) and via the enzymatic detoxification pathway (increase in HO-1 synthesis).

Atmospheric pollutants, such as particulate matter or gaseous pollutants such as sulfur dioxide, ozone and nitrogen oxides, or cigarette smoke, have an initiator activity on free radicals which are the source of oxidation phenomena causing cell damage in living beings. The cells of organs which are in direct and permanent contact with the outside environment, such as the skin, the scalp and certain mucous membranes, are particularly sensitive to these effects of the pollutants, which result in particular in accelerated aging of the skin, with a complexion which lacks radiance, pigment spots and early formation of wrinkles and fine lines, and also in a decrease in the vigor and a dull appearance of the hair.

The invention thus relates to the use of the combination (or the compositions containing same), for combatting the signs of aging of the skin or of the skin appendages, whether said aging is intrinsic or extrinsic, and for combatting the cutaneous signs linked to the effect of the environment and of pollution.

In addition to the wrinkles and fine lines, the appearance of pigment spots, decreased skin thickness, loss of skin elasticity and sagging of the skin are also changes observed during aging. In addition to its continuous aging, the skin constantly changes as a function of the individual's state of fatigue, which results in signs such as bags and dark circles under the eyes, drawn features and a dull complexion.

The combination, or a composition containing same, will in particular be of use for decreasing or preventing skin disorders such as a dull appearance of the complexion, hyperpigmentation of the skin or heterogeneity of the pigmentation thereof and pigment spots, wrinkles and fine lines, thinning of the skin and loss of firmness and/or of elasticity of the skin.

The term "skin" is intended to mean facial and/or bodily skin, the scalp and the mucous membranes or semi-mucous membranes (for instance the lips). The term "skin appendages" is intended to mean the hair, body hairs, eyelashes, nails, and preferably the hair.

Moreover, the presence of dark circles under the eyes is a sign which contributes to an appearance of fatigue or of aging, and it is desirable to reduce them. Among the causes responsible for their presence, mention may be made of an accumulation of hemoglobin in the thin and highly vascularized area located under the eye. The stimulation of hemoglobin degradation in this region contributes to the disappearance of the dark areas and thus to the reduction or disappearance of the dark circles.

A subject of the invention is thus also the use of the combination of a spruce extract and of polyphenols according to the invention, or the compositions containing same, for improving the radiance of the skin and of the complexion and/or preventing or reducing the appearance of dark circles around and/or under the eyes.

The invention also relates to the use of a spruce or *Picea abies* extract as defined in the present text, for preventing or reducing the presence of dark circles under the eyes.

In the present description, for the ranges expressed "between . . . and . . . " or "from . . . to . . . ", it is understood that the limits are included.

Spruce or common spruce (*Picea abies*) is a species of resinous trees of the family Pinaceae and of the genus *Picea*. The extracts suitable for implementing the invention are preferably obtained from the wood and from the bark of the tree, in particular from the wood present in the knots of the wood or in the area neighboring the knots.

The spruce extracts for the implementation of the invention preferably contain at least 5%, and in particular between 5% and 15%, of lignans relative to the weight of the extract (expressed as solids), with at least one lignan chosen from: hydroxymatairesinol, secoisolariciresinol, conidendrin, lariciresinol and liovil. An extract that is particularly suitable for the implementation of the invention contains at least 4%, especially between 4% and 10% and in particular approximately 5% to 6% of hydroxymatairesinol. The content of each of the other lignans in the extract is generally between 0.01% and 5%, and in particular approximately 0.1 to 2%. An extract (with an 8% lignan content) dissolved in glycerol is in particular used.

The polyphenols that are suitable for implementing the invention are chosen from proanthocyanidin monomers and oligomeric proanthocyanidins (OPCs), hydroxystilbenes, and flavonoid monomers and oligomers. Such polyphenols are for example extracted from various plants, and in particular from vine. They can be obtained from various parts of the *Vitis vinifera* plant, for example from the fruits or from parts of the fruits such as the seeds or the skin, but also from the vine shoots.

The polyphenols may in particular be chosen from hydroxystilbenes in monomer or oligomer form, and in particular resveratrol (in cis and/or trans form), rhapontin, deoxyrhapontin, piceatannol, piceid and viniferins.

Other polyphenols that are suitable for the invention are flavonoids, such as monomers and oligomers of flavan-3-ols, in particular catechin, epicatechin, gallocatechins, epigallocatechins (for example epigallocatechin gallate) and oligomeric proanthocyanidins or OPCs, anthocyanins or flavanones; mention may also be made of flavonols, dihydroflavonols, flavones and isoflavones.

Advantageously, the polyphenols or the polyphenol derivatives comprise resveratrol and/or catechins, and/or catechin or resveratrol oligomers, or derivatives of these compounds.

The catechin oligomers preferably comprise from 2 to 6 catechic (catechin or epicatechin) units and are also known as OPCs.

These polyphenols may be in native or stabilized form.

The term "polyphenol derivatives" is intended to mean more particularly stabilized molecules in which all or some of the hydroxyl groups are etherified or esterified. According to one preferred embodiment, the esterification is formed with a saturated or unsaturated fatty acid. The fatty acid may in particular be chosen from butyric, valeric, hexanic, sorbic, lauric, palmitic, stearic, oleic, linoleic, linolenic, alpha-linolenic, arachidonic, ecosapentaenoic and docosahexaenoic acid.

The monomer units of the flavonoids correspond to structure (I) below

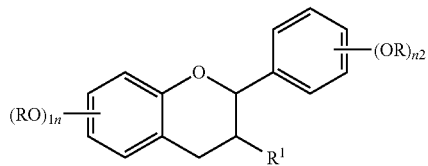

(I)

in which —R1 represents an —OR2 group, a hydrogen atom or a substituent R3; R2 and R3, which may be identical or different, being as defined below for R4, at least the majority of the substituents R represent a —COR4 group, R4 being a linear or branched, saturated or unsaturated alkyl radical having at least two carbon atoms, or an aryl, arylalkyl or arylalkylene radical, the other substituent(s) R which do not represent a —COR4 group being a hydrogen atom or an alkyl group, and n1 and n2, which may be identical to or different than one another, are numbers from 1 to 3, corresponding to the number of substituents on a ring, the monomer units being linked in the oligomers and the polymers by carbon-carbon bonds and/or an ether bridge between the units.

In the oligomers and polymers of the invention, the bonds between the carbon atoms of the successive units are located between the C-4 of one unit and the C-6 or the C-8 of another unit.

In other oligomers and polymers, at least two units are also linked by an oxygen bridge.

In one corresponding composition, the polyphenol oligomers or polymers correspond to the formula

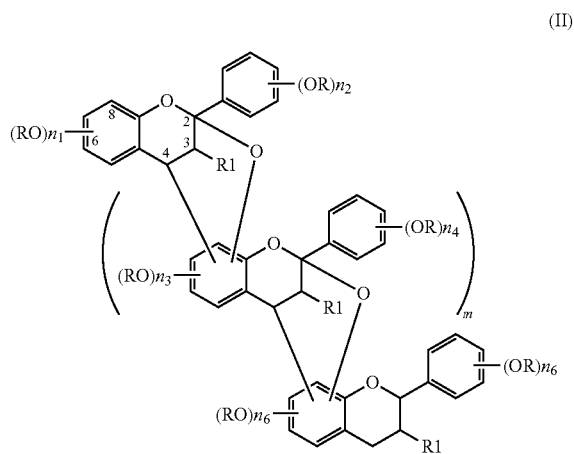

(II)

in which R1 and R are as defined above, n1 to n6, which may be identical or different, are numbers from 1 to 3 and m is a number from 0 to 100, more particularly from 1 to 10.

In formula (II), m is preferably a number from 11 to 100 or, in one variant, m is equal to 0.

The invention is in particular directed toward a composition characterized in that R represents a saturated or unsaturated fatty acid radical chosen more especially from the group comprising butyric, valeric, hexanic, sorbic, lauric, palmitic, stearic, oleic, linoleic, linolenic, α-linolenic, arachidonic, ecosapentaenoic and docosahexaenoic acid radicals.

In yet other polyphenols of formula (II), R2 represents a phenyl or arylalkyl or arylalkylene group, the alkyl or alkylene radical being more particularly $C_1$ to $C_8$, in particular $C_1$ to $C_4$. By way of example of arylalkyl or arylalkylene groups, mention will be made of the benzyl group and the styryl group.

The invention is in particular directed toward flavanol derivatives, in particular those in which R1 is an —OR2 group, R2 being as defined above. It is preferably a question of esters of flavanol derivatives belonging to the catechic series.

In these esters, there are generally five oxygen-bearing groups per flavanol unit, and said groups are in positions 3, 5, 7, 3' and 4'.

In one preferred composition, the polyphenols are flavonoid extracts of plant sources, in particular of vine and more especially of grapeseeds (OPCs), containing monomers, oligomers and/or polymers of units corresponding to formula (I).

According to a second aspect, the polyphenols used in the combinations of the invention are stilbenoic extracts of plant sources, in particular of vine and more especially of vine shoots, containing monomers, oligomers and/or polymers of units corresponding to formula (III)

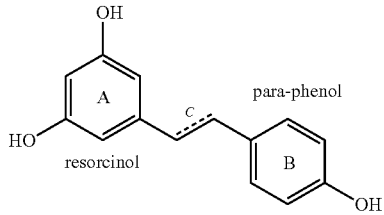

(III)

These units are characterized by the simultaneous presence of a nucleus of resorcinol type (nucleus A) and of a nucleus of para-phenol type (nucleus B), linked to one another by a carbon-based linker such as C. In the simplest case, the two nuclei A and B are combined and the segment C does not exist, which corresponds to the case of phloroglucinol. The nuclei A and B of these units are usually distinct, and the segment C consists of two carbons which may be sp2-hybridized and form a vinyl: this is the case of resveratrol.

The segment C may just as easily consist of sp3-hybridized carbons and may serve, in particular, as a point of attachment between the monomers in order to form the polymers. Like flavonoids, these stilbene compounds are stabilized by —OR groups (corresponding to the esterification of the —OH functions).

The invention is also directed toward a composition characterized in that the polyphenols correspond to the diastereoisomers and/or to the regioisomers of said flavonoid and stilbene polyphenols.

According to one particular embodiment, all of the hydroxyl groups of the polyphenol are esterified or etherified; the polyphenol derivative thus no longer has a free OH function.

Such ethers or esters may in particular be prepared by means of the process described in application WO 2011/128714.

Polyphenols extracted from vine shoots, in particular resveratrol, and derivatives thereof, are in particular used. Polyphenols that are particularly suitable for implementing the invention are catechins, catechin oligomers or OPCs, such as those extracted from grapeseeds, and derivatives of these polyphenols, in particular esters thereof.

It is understood that, in the context of the invention, the mixtures in any proportions of the various polyphenols and of the derivatives thereof, which may be partially or totally esterified or etherified, as defined in the aforementioned, may be used.

Advantageously, in one composition according to the invention, the polyphenols mentioned in (a) are extracted from vine, and comprise OPCs extracted from grapeseed; in particular, the combination or the composition comprises polyphenol derivatives which are polyphenol esters.

According to one particular embodiment, the polyphenols are present in the combination or the composition in the form of grapeseed extracts, optionally stabilized so as to obtain polyphenol derivatives in said extracts.

Such polyphenols generally comprise at least 20% (by weight, relative to the weight of total polyphenols) of catechin monomers and/or dimers; for example, the proanthocyanidin dimer content is greater than or equal to 20% (by weight, relative to the weight of total polyphenols), and/or the [catechin and epicatechin] content is greater than or equal to 20% (by weight, relative to the weight of total polyphenols).

According to one embodiment of the invention, the grapeseed extracts are essentially free of components other than polyphenols.

A composition, in particular a cosmetic composition, according to the invention may in particular comprise polyphenols or the polyphenol derivatives mentioned in (a) in a concentration of from 0.01% to 10% by weight relative to the total weight of the composition, and in particular greater than or equal to 0.05%. According to one embodiment of the invention, in the composition, the polyphenols or the polyphenol derivatives mentioned in (a) are present for example at a concentration of from 0.1% to 5%; in particular, the composition contains from 0.1% to 5% of esterified derivatives of grapeseed polyphenols.

A composition, in particular a cosmetic composition, according to the invention may in particular comprise the spruce extract, in particular a spruce wood extract present at a concentration of from 0.01% to 10% by weight relative to the total weight of the composition. The spruce extract may for example be present at a concentration of greater than or equal to 0.05%, and in particular greater than or equal to 0.1%. The spruce wood extracts as defined in the aforementioned may thus be present at a concentration of from 0.1% to 5%, or even from 0.5% to 5% or from 0.5% to 3% by weight relative to the total weight of the composition.

A composition according to the invention contains for example a grapeseed extract, optionally stabilized by esterification of the polyphenols, at a concentration of from 0.01% to 10% by weight relative to the total weight of the composition and a spruce wood extract present at a concentration of from 0.01% to 10% by weight relative to the total weight of the composition, for example at a concentration of greater than or equal to 0.05%.

Advantageously, in a cosmetic composition according to the invention, the weight ratio between the polyphenols, in particular the polyphenols extracted from vine (in particular the grapeseed polyphenols, rich in OPCs) or derivatives thereof and the spruce extract is from 0.1% to 5% expressed as polyphenols/spruce lignans (or as polyphenols extracted from vine/spruce lignans) and preferentially a grape polyphenols/spruce lignans ratio of between 0.5 and 3. This is because it has been observed that, in these ratios, the synergistic activity on the endogenous antioxidant defenses mediated by the HO-1 enzyme is optimal.

In particular, on human skin fibroblasts, HO-1 synthesis is increased by at least 30%, in particular by at least 40%, compared to the increase that would be expected by a simple effect of adding each of the two components of the combination; this synergy may result in an increase of more than 70% compared with the sum of the effects of each of the components of the combination.

The compositions according to the invention are preferably cosmetic compositions, or dermatological compositions suitable for application to the skin or the skin appendages. The composition according to the invention contains the combination of polyphenols and spruce extracts as defined above, and a physiologically acceptable medium.

The term "physiologically acceptable medium" is intended to mean a medium compatible with the skin or the skin appendages. It is in particular a cosmetically acceptable medium. It is thus intended to mean a medium or excipients that are well tolerated by the skin and that have a pleasant odor and appearance.

The term "cosmetic product or composition" is intended to mean a substance or a mixture intended to be brought into contact with the surface parts of the human body or with the teeth and the buccal mucous membranes, for the purpose, exclusively or mainly, of cleaning them, of fragrancing them, of modifying the appearance thereof, of protecting them, of maintaining them in good condition or of correcting body odors.

This composition may be more or less fluid and may have the appearance of a white or colored cream, of an ointment, of a milk, of a lotion, of a serum, of a paste or of a foam. It may also be in solid form, in particular in the form of a stick. It may be used as a care product and/or as a makeup product and/or a hygiene product for the skin or the skin appendages.

The composition according to the invention may be in any of the pharmaceutical forms normally used in the cosmetics field, and it may in particular be in the form of an optionally gelled aqueous or oily solution, of a dispersion of the optionally two-phase lotion type, of an emulsion obtained by dispersion of a fatty phase in an aqueous phase (O/W) or vice-versa (W/O), or of a triple emulsion (W/O/W or O/W/O) or of a vesicular dispersion of ionic and/or nonionic type. These compositions are prepared according to the usual methods.

When the composition used according to the invention is an emulsion, the proportion of the fatty phase may range from 0.5% to 80% by weight, and preferably from 5% to 50% by weight, relative to the total weight of the composition. The oils, the emulsifiers and the co-emulsifiers used in the composition in emulsion form are chosen from those conventionally used in the field in question. The emulsifier and the co-emulsifier are present, in the composition, in a proportion ranging from 0.1% to 30% by weight, and preferably from 0.5% to 20% by weight, relative to the total weight of the composition.

As oils that can be used in the invention, mention may be made of hydrocarbons or mineral origin (mineral oil) or synthetic origin (liquid petroleum jelly, isohexadecane), oils of plant origin (apricot kernel oil, grapeseed oil, liquid fraction of shea butter, avocado oil, soya oil), oils of animal origin (lanolin), synthetic oils (perhydrosqualene, pentaerythrityl tetraoctanoate), silicone derivatives (cyclopentasiloxane, cyclohexasiloxane and silicone polymers) and fluoro oils (perfluoropolyethers). Use may also be made, as fatty substances, of fatty alcohols (cetyl or stearyl alcohol), fatty acids (stearic acid), waxes (carnauba wax, ozokerite, beeswax), butters and hydrogenated oils.

As emulsifiers and co-emulsifiers that can be used in the invention, mention may for example be made of fatty acid esters of polyethylene glycol, such as PEG-100 stearate and PEG-20 stearate, and fatty acid esters of glycerol, such as glyceryl stearate, sucrose esters and phospholipids.

In a known manner, the composition used according to the invention may also contain the adjuvants usual in the cosmetics field, such as hydrophilic or lipophilic gelling agents, hydrophilic or lipophilic active agents, preservatives, antioxidants, solvents, fragrances, fillers, screening agents, pigments, odor absorbers, chelating agents and dye stuffs. The amounts of these various adjuvants are those conventionally used in the field in question, and for example from 0.01% to 20% of the total weight of the composition. Depending on their nature, these adjuvants may be introduced into the fatty phase, into the aqueous phase or in lipid vesicules. In any event, these adjuvants, and also the proportions thereof, will be chosen so as not to harm the desired properties of the antioxidant combination.

As hydrophilic gelling agents, mention may in particular be made of carboxyvinyl polymers (carbomer), acrylic copolymers such as acrylate/alkyl acrylate copolymers, polyacrylamides, polysaccharides, natural gums and clays, and, as lipophilic gelling agents, mention may be made of modified clays such as bentones, metal salts of fatty acids, hydrophobic silica and polyethylenes.

As fillers, mention may for example be made of particles of polyamide (Nylon) in spherical form or in the form of microfibers; poly(methyl methacrylate) microspheres; ethylene/acrylate copolymer powders; expanded powders such as hollow microspheres, and in particular the microspheres formed from a terpolymer of vinylidene chloride, of acrylonitrile and of methacrylate and sold under the name Expancel by the company Kemanord Plast; powders of natural organic materials, such as starch, in particular corn starch, wheat or rice powders, which may or may not be crosslinked, such as octenyl succinate anhydride-crosslinked starch powders; silicone resin microbeads such as those sold under the name Tospearl by the company Toshiba Silicone; silica; metal oxides such as titanium dioxide or zinc oxide; mica; and mixtures thereof.

The composition used according to the invention may also contain other active agents, and in particular at least one compound chosen from: moisturizing agents; depigmenting agents; antiglycation agents; NO-synthase inhibitors; agents which stimulate the synthesis of dermal or epidermal macromolecules and/or which prevent degradation thereof; agents which stimulate fibroblast and/or keratinocyte proliferation or which stimulate keratinocyte differentiation; muscle-relaxing agents; tensioning agents; antipollution agents and/or free-radical scavengers, sunscreens, and mixtures thereof.

As antioxidants, mention may in particular be made of tocopherol and esters thereof, in particular tocopheryl acetate; ascorbic acid and derivatives thereof, in particular ascorbyl magnesium phosphate, ascorbyl glucoside and ascorbyl tetraisopalmitate; ferulic acid; serine; ellagic acid, phloretin, chelating agents, such as BHT, BHA, or N,N'bis (3,4,5-trimethoxybenzyl)ethylenediamine and salts thereof, and mixtures thereof.

In particular, the cosmetic composition according to the invention also contains at least one active agent chosen from vitamin C and derivatives thereof and vitamin E or derivatives thereof such as tocopheryl acetate.

The additional active agents may be present in the composition according to the invention in a content ranging from 0.001% to 20% by weight relative to the total weight of the composition, preferably from 0.01% to 10%, even more preferentially from 0.5% to 5% and more preferably from 0.1% to 1% by weight, relative to the total weight of the composition.

A subject of the invention is also a cosmetic treatment process comprising a step of applying, to the skin or the skin appendages, the combination or the compositions according to the invention.

It is in particular a cosmetic treatment process for preventing or decreasing skin disorders induced by oxidative stress, comprising at least one step consisting in applying, to the skin or the skin appendages, a combination of at least (a) one polyphenol chosen from proanthocyanidin monomers and oligomeric proanthocyanidins (OPCs), hydroxystilbenes, flavonoid monomers and oligomers, derivatives thereof and mixtures thereof, and (b) one spruce extract comprising at least one lignan chosen from hydroxymatairesinol, secoisolariciresinol, conidendrin, lariciresinol and liovil, or a cosmetic composition containing said combination.

The cosmetic treatment process will thus aim to prevent or decrease the cutaneous signs such as a dull appearance of the complexion, hyperpigmentation of the skin or heterogeneity of the pigmentation thereof and pigment spots, wrinkles and fine lines, thinning of the skin and loss of firmness and/or of elasticity of the skin.

The cosmetic treatment process will also be of use for improving the radiance of the skin and of the complexion and/or preventing or decreasing the appearance of dark circles around and/or under the eyes, by applying a spruce extract, a combination containing same or compositions as defined in the aforementioned.

The compositions according to the invention may be applied directly to the skin or, alternatively, to cosmetic or dermatological supports of occlusive or nonocclusive type, intended to be applied in a localized manner to the skin, such as hydrogel masks, wipes, fabrics, or biocellulose.

The application may for example be daily, several times a day or weekly. It may be continued for several days and/or several weeks, or even longer; it may be continuous or alternatively, for example, continued for 1 to 2 months and then recommenced after an interruption.

The invention also relates to the use of a combination of
(a) at least one polyphenol chosen from proanthocyanidin monomers and oligomeric proanthocyanidins (OPCs), hydroxystilbenes, flavonoid monomers and oligomers, derivatives thereof and mixtures thereof,
(b) a spruce extract comprising at least one lignan chosen from: hydroxymatairesinol, secoisolariciresinol, conidendrin, lariciresinol and liovil as defined in the present text, for preparing a cosmetic composition.

The composition is suitable for application to the skin or the skin appendages. The composition advantageously makes it possible to combat the signs associated with the action of free radicals on the skin or the skin appendages.

The invention further relates to a process for preparing a cosmetic composition, comprising a step in which the following are mixed:
(a) at least one polyphenol chosen from proanthocyanidin monomers and oligomeric proanthocyanidins (OPCs), hydroxystilbenes, flavonoid monomers and oligomers, derivatives thereof and mixtures thereof, and
(b) a spruce extract comprising at least one lignan chosen from: hydroxymatairesinol, secoisolariciresinol, conidendrin, lariciresinol and liovil,
and optionally a physiologically acceptable excipient.

Other features and advantages of the invention are illustrated in the examples which follow.

Example 1: Activity of a *Picea Abies* Extract on the Antioxidant Defenses

A confluent culture of human fibroblasts at 37° C., in DMEM medium supplemented with 1% of fetal calf serum, is treated with various concentrations of *Picea abies* extract.

A *Picea abies* extract having the following lignan composition (% by weight) is tested:

| | |
|---|---|
| Total lignans: | 6-8.4% |
| Hydroxymatairesinol | 5-6% |
| Secoisolariciresinol | 0.3-0.4% |
| Conidendrin | 0.2-0.4% |
| Liovil | 0.2-0.4% |
| Lariciresinol | 0.1-0.2% |
| Other lignans | 0.2-1%. |

Quantification of GSH in the cell lysates

The GSH/GSSG-Glo test is based on a system of luminescence for detecting and quantifying total glutathione (GSH+GSSG), GSSG and the GSH/GSSG ratio. The determination is based on a reaction for conversion of a luciferin-NT probe into luciferin by a glutathione S-transferase enzyme coupled with a reaction with luciferase. The luminescence detected is proportional to the amount of GSH present.

In one case, the total amount of glutathione is measured. For this, all of the glutathione present in the cell lysate is converted into GSH, which is then measured by the test. In the case where only the GSSG oxidized form is measured, the GSH present is blocked by a reagent before converting the GSSG into GSH.

After incubation, the cell culture medium is removed and the cells are washed with PBS, which is then replaced with lysis buffer.

The cells are lysed for 5 min at ambient temperature.

50 µl of "luciferin-generating medium" are added.

The plates are incubated at ambient temperature for 30 min.

100 µl/well of detection reagent were added.

The plates were equilibrated for 15 min at ambient temperature.

The luminescence is measured with a Tecan M200 instrument with the following parameters: integration time=1 s, resting time=1 s.

Result: The *Picea abies* extract at concentrations ranging from 100 to 500 µg/ml (0.01%-0.05%) significantly increases the synthesis of cell GSH in normal human dermal fibroblasts starting from 11% up to 66% relative to the basal level of the non-treated cells.

These data were confirmed in a second experiment which showed that a *Picea abies* extract rich in hydroxymatairesinol at concentrations ranging from 250-500 µg/ml (0.025%-0.05%) is capable of inducing a significant cell synthesis of GSH in normal human dermal fibroblasts starting from 33% up to 64% relative to the basal level of the non-treated cells.

The absence of cell toxicity under these experimental conditions was moreover verified and makes it possible to conclude that the effect observed on the defense stimulation is not the result of a toxic effect.

Quantification of the HO-1 enzyme in cell lysates

After 24 h of stimulation with the compounds, the cells were detached, centrifuged for 10 min at 1200 rpm and resuspended in lysis buffer. Two cycles of freezing in liquid nitrogen/thawing were carried out and then the cell fragments were removed by centrifugation. The cell lysates are then stored at −80° C. before use.

The total protein concentrations in samples were determined using the BCA kit (Sigma) according to the producers instructions. For each sample, the measurement was carried out in triplicate. The mean value is reported in the results presented.

The amount of HO-1 in the cell lysates was measured by means of an ELISA assay using the human total HO-1/HMOX1 ELISA kit, as follows:

ELISA plates were coated with capture antibodies at the concentration of 8 µg/ml and incubated at ambient temperature overnight.

The plates were washed three times with PBS-0.05% Tween 20 and blocked with PBS-1% BSA for 1 h at ambient temperature.

The plates were washed three times with PBS-0.05% Tween 20.

100 μl of non-diluted samples were added to plates and also HO-1 standard samples at concentrations ranging from 0.15-10 ng/ml. The incubation was carried out for 2 h at ambient temperature.

After three steps of washing with PBS-0.05% Tween 20, 100 μl of HRP-conjugated detection antibody (200 ng/ml) were added for 2 h at ambient temperature.

After three washing steps, a solution of streptavidin-HRP was added for 20 min at ambient temperature.

After three washing steps, the TMB HRP substrate was added. After an incubation time of 15-20 min, at ambient temperature and in the dark, the reaction was stopped by adding 2N $H_2SO_4$.

The optical density (OD) was read with the Tecan Infini microplate reader at 450 nm with correction at 570 nm.

The results were analyzed with the Magellan software.

The HO-1 concentrations were standardized with respect to a total protein concentration for each sample.

The absence of cell toxicity under these experimental conditions was moreover verified and makes it possible to conclude that the effect observed on the stimulation of the defenses is not the result of a toxic effect.

Results: HO-1 concentrations (pg/μg of total proteins)

|  | | Mean of the 3 samples | S.D. | p-value | Increase (%) |
|---|---|---|---|---|---|
| Nontreated | 0 | 11.75 | 0.54 | | |
| Picea abies extract at 8% (μg/ml) | 100 | 12.01 | 1.53 | 0.7973 | 2.19 |
| | 500 | 36.74 | 2.53 | <0.0001 | 212.63 |

Example 2: Activity of a Combination of an Extract of Picea abies and of Grapeseed on the Antioxidant Defenses A confluent culture of human fibroblasts at 37° C., in DMEM medium supplemented with 1% of fetal calf serum, is treated with various concentrations of *Picea abies* extract and of grapeseed extract, according to the same protocol as in example 1.

The grapeseed extracts have a proanthocyanidin content, relative to total polyphenols, as follows:

| Total polyphenols | 100% |
|---|---|
| Catechin + epicatechin | 22.6% |
| Proanthocyanidin dimers | 25.1% |

The HO-1 concentrations in the cell lysates were standardized with respect to the total protein concentration in each sample. The results are presented in the following table:

| | | HO-1 concentrations (pg/μg of total proteins) | | | |
|---|---|---|---|---|---|
| | | Mean of the 3 measurements | S.D | p value (t-test) | Increase (%) |
| Nontreated | 0 | 18.54 | 2.40 | | 0.00 |
| *Picea abies* extract at 8% (μg/ml) | 500 | 24.84 | 3.98 | 0.079 | 33.94 |
| Grapeseed extract (μg/ml) | 14.5 | 31.12 | 3.10 | 0.0052 | 67.83 |
| *Picea abies* extract at 8% + Grapeseed extract (μg/ml) | 500 + 14.5 | 65.90 | 9.36 | 0.0011 | 255.43 |

The absence of cell toxicity under these experimental conditions was moreover verified and makes it possible to conclude that the effect observed on the stimulation of the defenses is not the result of a toxic effect.

The percentage increase in the activity for an additive effect would have been 34%+68%, i.e. 102%. The activity measured for the combination of *Picea abies* extract and grapeseed extract is 76% greater than this theoretical sum.

This demonstrates that a grapeseed extract enriched with proanthocyanydins and a *Picea abies* extract rich in hydroxymatairesinol are capable of significantly inducing the production of the HO-1 antioxidant enzyme in normal human dermal fibroblasts in a synergistic manner. Indeed, the activity measured for the combination is greater than the sum of the activities measured for each compound individually.

The results are summarized in the table below:

| | | Enzymatic antioxidant defense: Increase in HO-1 (%) |
|---|---|---|
| *Picea abies* extract at 8% | 500 μg/ml | 34% |
| Grapeseed extract | 14.5 μg/ml | 68% |
| *Picea abies* extract at 8% + Grapeseed extract (theoretical activity for an additive effect) | 500 μg/ml + 14.5 μg/ml | 102% |
| *Picea abies* extract at 8% + Grapeseed extract | 500 μg/ml + 14.5 μg/ml | 255% |

Example 3: Compositions According to the Invention

| Lotion | |
|---|---|
| Common name | % |
| Water | QS 100 |
| Glycerol | 3.00 |
| Mixture of methylpropanediol, caprylyl glycol, phenylpropanol | 0.50 |
| *Picea abies* extract at 8% | 0.20 |
| Grapeseed polyphenols | 0.25 |
| Alcohol | 5.00 |

The various constituents of the composition are mixed so as to obtain a lotion. Said lotion will be applied in the morning and/or the evening to all of the face and neck.

| Gel cream | |
|---|---|
| Common name | % |
| Water | QS 100 |
| Butylene glycol | 3.00 |
| C10/30 alkyl acrylates crosspolymer | 0.50 |
| Xanthan gum | 0.30 |
| Coco-caprylate | 5.00 |
| Grapeseed oil | 3.00 |
| *Picea abies* extract at 8% | 1.00 |
| Vine polyphenol derivatives | 0.60 |
| Potassium sorbate | 0.20 |
| Fragrance | 0.30 |

The gel cream will be applied in the morning and/or the evening to the face, the neck and the hands.

| Emulsion | |
|---|---|
| Common name | % |
| Water | QS 100 |
| C10/30 alkyl acrylates crosspolymer | 0.30 |
| Phytic acid | 0.05 |
| Mixture of methylpropanediol, caprylyl glycol, phenylpropanol | 2.00 |
| Dicaprylyl ether | 20.00 |
| Mixture of cetearyl alcohol and PEG-20 stearate | 3.00 |
| *Picea abies* extract at 8% | 1.00 |
| Vine polyphenol derivatives | 0.3 |

The composition will be applied in the morning and/or the evening to the face and the neck.

The invention claimed is:

1. An antioxidant cosmetic composition for skin and/or hair containing
(a) polyphenols extracted from grapeseed and comprising proanthocyanidin dimers, catechin, and epicatechin, said polyphenols being stabilized by esterification,
(b) a *Picea abies* spruce extract comprising hydroxymatairesinol, and
(c) at least one active agent chosen from antioxidants, moisturizing agents, desquamating agents, agents which improve the barrier function, depigmenting agents, and agents which improve cutaneous microcirculation,
wherein said composition increases the production of the HO-1 antioxidant enzyme in normal human dermal fibroblasts by more than the sum of said production for each of said polyphenols (a) and said *Picea abies* spruce extract (b).

2. The cosmetic composition according to claim 1, wherein the polyphenols are present at a concentration of from 0.01% to 10% by weight relative to the total weight of the composition.

3. The cosmetic composition according to claim 1, wherein the spruce extract is present at a concentration of from 0.01% to 10% by weight relative to the total weight of the composition.

4. The cosmetic composition according to claim 1, wherein
(a) the polyphenols are present at a concentration of from 0.01% to 10% by weight relative to the total weight of the composition, and
(b) the *Picea abies* spruce extract is present at a concentration of from 0.01% to 10% by weight relative to the total weight of the composition.

5. The cosmetic composition according to claim 1, wherein a weight ratio of concentrations between the polyphenols extracted from grapeseed and the spruce extract is between 0.1 and 5 expressed as polyphenols/spruce lignans.

6. The cosmetic composition according to claim 1, wherein the at least one active agent is chosen from vitamin C and derivatives thereof and vitamin E and derivatives thereof.

7. A method for combatting the signs of aging of the skin or of the skin appendages or combatting the cutaneous signs linked to pollution comprising applying the composition of claim 1 to skin.

8. A method for improving the radiance of the skin and/or decreasing the appearance of dark circles around the eyes comprising applying the composition of claim 1 to skin.

9. The method according to claim 7, wherein the composition is applied as an agent for combatting a disorder chosen from wrinkles and fine lines, a dull complexion, pigment spots, the loss of firmness of the skin, and dark circles under the eyes.

10. A cosmetic treatment process for preventing or decreasing skin oxidative stress, comprising the step of applying, to the skin or the scalp, the composition of claim 1.

11. A method for improving radiance of the skin and/or for preventing or decreasing presence of dark circles under the eyes, comprising the step of applying the composition of claim 1 to the skin.

12. A cosmetic composition for skin and/or hair comprising
about 0.01 to about 10% by weight grapeseed extract polyphenols comprising catechin, epicatechin and proanthocyanidin dimers, said polyphenols being stabilized by esterification,
about 0.01 to about 1.0% by weight *Picea abies* extract comprising hydroxymatairesinol, and
a cosmetically acceptable carrier
wherein the composition increases the production of HO-1 antioxidant enzyme in normal human dermal fibroblasts by more than the sum of said production for each of said polyphenols (a) and said *Picea abies* spruce extract (b).

13. The cosmetic composition of claim 1, wherein said spruce extract further comprises secoisolariciresinol, conidendrin, lariciresinol and liovil.

14. The antioxidant cosmetic composition of claim 1, wherein the proanthocyanidin dimers comprise greater than or equal to 20% by weight, relative to the weight of total polyphenols, and the catechin and epicatechin comprise greater than or equal to 20% by weight, relative to the weight of total polyphenols.

15. The antioxidant cosmetic composition of claim 1, wherein the *Picea abies* spruce extract comprises at least 4% hydroxymatairesinol.

16. The antioxidant cosmetic composition of claim 15, wherein the *Picea abies* spruce extract comprises between 4% and 10% hydroxymatairesinol.

17. The cosmetic composition for skin and/or hair of claim 12, wherein the proanthocyanidin dimers comprise greater than or equal to 20% by weight, relative to the weight of total polyphenols, and the catechin and epicatechin comprise greater than or equal to 20% by weight, relative to the weight of total polyphenols.

18. The cosmetic composition for skin and/or hair of claim 12, wherein the *Picea abies* spruce extract comprises at least 4% hydroxymatairesinol.

19. The cosmetic composition for skin and/or hair of claim 18, wherein the *Picea abies* spruce extract comprises between 4% and 10% hydroxymatairesinol.

20. An antioxidant cosmetic composition for skin and/or hair comprising
   about 14.5 µg/ml esterified derivatives of grapeseed extract polyphenols comprising catechin, epicatechin and proanthocyanidin dimers and having the proanthoycyandin dimer content greater than or equal to 20% by weight relative to weight of total polyphenols,
   about 100-500 µg/ml *Picea abies* extract that comprises about 5% to 6% of hydroxymatairesinol, and
   a cosmetically acceptable carrier.

* * * * *